United States Patent [19]

Fahey et al.

[11] 4,180,525
[45] Dec. 25, 1979

[54] TRANS-HALO(ACYL)BIS(TRIETHYLPHOSPHINE) NICKEL(II) COMPLEXES

[75] Inventors: Darryl R. Fahey; John E. Mahan, both of Bartlesville, Okla.

[73] Assignee: Phillips Petroleum Company, Bartlesville, Okla.

[21] Appl. No.: 930,615

[22] Filed: Aug. 3, 1978

Related U.S. Application Data

[62] Division of Ser. No. 739,763, Nov. 8, 1976, Pat. No. 4,123,447.

[51] Int. Cl.$^2$ .............................................. C07C 3/21
[52] U.S. Cl. ................................................... 585/523
[58] Field of Search ............................... 260/683.5 D

[56] References Cited

U.S. PATENT DOCUMENTS

| | | | |
|---|---|---|---|
| 3,636,128 | 1/1972 | Dunn et al. | 260/683.15 D |
| 3,689,588 | 9/1972 | Dunn | 260/683.15 D |
| 3,800,000 | 3/1974 | Fahey | 260/666 PY |
| 3,808,246 | 4/1974 | Fahey | 260/439 R |
| 3,907,923 | 9/1975 | Yoo | 260/683.15 D |
| 4,000,211 | 12/1976 | Smith et al. | 260/683.15 D |

OTHER PUBLICATIONS

Chem. Abs. 79 66547w (1973).
J.C.S., Dalton, 2216 (1974).
J.A.C.S. 95 (10) 3180 (1973).
Organometal Chem. Rev. A, 7, 245, 270, 271 (1972).
*The Organic Chemistry of Nickel,* Jolly et al., Academic Press (1974), pp. 170 & 171.
J.C.S. Chem. Comm. 396 (1972).
J.C.S. (A), 3019 (1969).
J.A.C.S., 99, 2501 (1977).

*Primary Examiner*—C. Davis

[57] ABSTRACT

A process for oligomerizing monoolefins using a catalyst system comprising at least one organoaluminum halide and at least one trans-halo(acyl)bis(triethylphosphine) nickel(II) complex.

10 Claims, No Drawings

TRANS-HALO(ACYL)BIS(TRIETHYLPHOSPHINE) NICKEL(II) COMPLEXES

This application is a divisional application of Ser. No. 739,763, filed Nov. 8, 1976, now U.S. Pat. No. 4,123,447.

This invention relates to nickel complex compositions. In another aspect this invention relates to methods of preparing and using nickel complex compositions. In a further aspect this invention relates to acyl nickel complexes.

Methods are known in the art for the dimerization of olefinic hydrocarbons in the presence of a catalyst system containing a nickel complex. Dimerization of propylene and other lower monoolefins continues to be of interest in the synthesis of monomers for addition polymerization, as intermediates in alcohol production by the oxo process, and as intermediates in the manufacture of plasticizers, lube additives, monomers for condensation polymerization, detergent base materials, improved motor fuel and the like. This continuing interest has established a need in the art for improved nickel complex dimerization catalysts. The extent of the dimerization, as well as stability of the resulting catalyst, is greatly dependent upon the character of the components employed to produce the catalyst system. In general, substantial variations in resulting dimer product types, catalyst stability, and olefin conversion are encountered if the character of the catalyst complex is varied.

It is an object of the present invention to provide heretofore unknown acyl nickel complexes.

A further object of the present invention is to provide methods for preparing heretofore unknown acyl nickel complexes.

A still further object of this invention is to provide a process for oligomerizing monoolefins employing said heretofore unknown acyl nickel complexes.

Other aspects, objects, and advantages of the invention will be apparent to one skilled in the art from this disclosure and the appended claims.

In accordance with the present invention trans-halo(acyl)bis(triethylphosphine)nickel(II) complexes are provided which have the formula

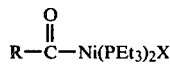

wherein X is a halogen; PEt₃ is triethylphosphine; and R is selected from the group consisting of alkyl hydrocarbon radicals containing 1 to 12 carbon atoms; aryl hydrocarbon radicals containing 6 to 12 carbon atoms; substituted aryl radicals containing 6 to 12 carbon atoms and having as the only non-hydrocarbon substituents 1 or 2 halogens selected from fluorine, chlorine, and bromine bonded to the aromatic portion of the aryl radical; and substituted aralkyl radicals containing 7 to 12 carbon atoms and having as the only non-hydrocarbon substituents one or more halogens selected from fluorine, chlorine, and bromine bonded to the aromatic portion of the aralkyl radical. Examples of such complexes include trans-chloro(1-adamantanecarbonyl)bis(triethylphosphine)nickel(II), trans-chloro(pivaloyl)bis(triethylphosphine)nickel(II), trans-chloro(4-chlorobenzoyl)bis(triethylphosphine)nickel(II), trans-chloro(3-chlorobenzoyl)bis(triethylphosphine)nickel(II), trans-chloro(benzoyl)bis(triethylphosphine)nickel(II), trans-chloro(3,3-dimethylbutanoyl)bis(triethylphosphine)nickel(II), trans-chloro(2-chlorobenzoyl)bis(triethylphosphine)nickel(II), trans-chloro(acetyl)bis(triethylphosphine)nickel(II), trans-bromo(benzoyl)bis(triethylphosphine)nickel(II), trans-fluoro(benzoyl)bis(triethylphosphine)nickel(II), and trans-chloro(1-naphthoyl)bis(triethylphosphine)nickel(II).

One method of preparing trans-halo(acyl)bis(triethylphosphine)nickel(II) complexes having the formula set forth in the preceding paragraph involves reaction in solution of 1,5-cyclooctadiene)bis(triethylphosphine)nickel(O), also referred to herein as Ni(1,5-COD) (PEt₃)₂, with acyl halides of the formula

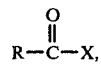

wherein R and X are as described in the preceding paragraph, under reaction conditions suitable for producing the corresponding trans-halo(acyl)bis(triethylphosphine)nickel(O) complexes. In this reaction any solvent can be employed which does not prevent the formation of the desired product. The amount of solvent needed is generally that amount which will insure that the reactants are in the liquid phase at the reaction temperature. One skilled in the art having the benefit of this disclosure can readily vary the concentration of reactants in various suitable solvents to obtain different reaction rates and yields of products. Examples of suitable solvents include aliphatic hydrocarbons, aromatic hydrocarbons, ethers, aliphatic nitriles, aliphatic ketones, alkyl esters of aliphatic acids, and mixtures of any two or more thereof. Typical examples of solvents include hexane, heptane, cyclohexane, octane, benzene, toluene, xylenes, dioxane, diethyl ether, tetrahydrofuran, diethylene glycol dimethyl ether, acetonitrile, propionitrile, butyronitrile, acetone, methylethyl ketone, diethyl ketone, methyl acetate, ethyl acetate, methyl propionate, and mixtures of any two or more thereof.

The Ni(1,5-COD)(PEt₃)₂ employed can be prepared in any suitable manner. A preferred embodiment of this method of preparing the subject trans-halo(acyl)bis(triethylphosphine)nickel(II) complexes involves employing the product mixture which results on mixing bis(1,5-cyclooctadiene)nickel(O) and triethylphosphine in a suitable solvent to produce Ni(1,5-COD) (PEt₃)₂ in situ. Suitable solvents include those set forth above for the reaction of Ni(1,5-COD) (PEt₃)₂ and an acyl halide. According to this preferred method, the product mixture comprising Ni(1,5-COD) (PEt₃)₂, 1,5-cyclooctadiene, and solvent is contacted with an acyl halide as above defined to give the corresponding trans-halo(acyl)bis(triethylphosphine)nickel(II) complex.

Any amounts of bis(1,5-cyclooctadiene)nickel(O) and triethylphosphine can be employed which result in the formation of significant amounts of Ni(1,5-COD) (PEt₃)₂. Generally the molar ratio of the former to the latter is in the range of about 4:1 to about 1:4, preferably about 1:2. Any temperature or pressure conditions can be employed which result in the formation of a solution of Ni(1,5-COD) (PEt₃)₂. The general and preferred conditions for temperature and pressure are the same as will be set forth below for the acylation reaction.

Examples of acyl halides falling within the formula

as above defined include benzoyl bromide, 4-toluoyl chloride, acetyl chloride, 3-chlorobenzoyl bromide, 1-adamantanecarbonyl chloride, benzoyl fluoride, 3-bromobenzoyl bromide, 3,3-dimethylbutanoyl chloride, pivaloyl chloride, 2-chlorobenzoyl chloride, 2,5-dichlorobenzoyl chloride, benzoyl chloride, 2,4-dimethyl benzoyl fluoride, 3-chloro-5-methyl benzoyl chloride, benzoyl iodide, 4-chlorobenzoyl chloride, 3-chlorobenzoyl chloride, 1-naphthoyl chloride, and 2,3-dimethyl-1-naphthoyl chloride.

Of course, two or more acyl halides can be employed to produce two or more different corresponding products. Those skilled in the art will however appreciate that such a course of action can present problems of competing reactions and can make recovery of the products more difficult.

While some product may be produced at higher or lower temperatures generally the temperature employed for reacting (1,5-cyclooctadiene)bis(triethylphosphine)nickel(O) and acyl halide is in the range of about $-50°$ C. to about $100°$ C., and preferably is in the range of about $0°$ C. to about $50°$ C. The pressure employed is generally that which will essentially maintain the solvent in the liquid phase at the reaction temperature, and preferably the reaction is conducted at atmospheric pressure. While longer or shorter reaction times can be employed, generally the reaction time is in the range of about 1 minute to about 2 hours, preferably about 2 minutes to about 30 minutes. Also while other molar ratios can be employed generally the molar ratio of the acyl halide, as defined above, to nickel(O) charged is in the range of about 5:1 to about 1:1, preferably 2:1 to about 1:1.

Preferably the acyl halide reactant should be in excess at all times during the mixing process to minimize the possibility of product decarbonylation by reaction of the product with any nickel(O) species present. Thus it is preferable to add the (1,5-cyclooctadiene)bis(triethylphosphine)nickel(O) or Ni(1,5-COD)$_2$/PEt$_3$ admixture to the acyl halide. Also it is preferable to (1) first prepare separate solutions of the nickel(O) triethylphosphine complex and the acyl halide and (2) then combine these solutions to produce the trans-halo(acyl)bis(triethylphosphine)nickel(II).

Some of the trans-halo(acyl)bis(triethylphosphine)nickel(II) complexes of this invention can also be prepared by the carbonylation of a solution of a Ni(II) complex of the formula R'—Ni(PEt$_3$)$_2$X under conditions sufficient to produce complexes of the formula

wherein for each formula X is a halogen; PEt$_3$ is triethylphosphine; and R' is selected from the group consisting of aryl hydrocarbon radicals containing 6 to 12 carbon atoms; substituted aryl radicals containing 6 to 12 carbon atoms and having as the only non-hydrocarbon substituents 1 or 2 halogens selected from fluorine, chlorine, and bromine bonded to the aromatic portion of the aryl radical; and substituted aralkyl radicals containing 7 to 12 carbon atoms and having as the only non-hydrocarbon substituents one or more halogens selected from fluorine, chlorine, and bromine bonded to the aromatic portion of the aralkyl radical. Examples of R' groups falling within the above description include phenyl, 4-tolyl, 4-chlorophenyl, 2,5-dichlorophenyl, 3-bromophenyl, 2-fluorophenyl, 3-chloro-5-methylphenyl, 2-tolyl, 4-bromophenyl, and 1-naphthyl.

The carbonylation reaction involves contacting the solution of the defined nickel(II) complex reactant with an amount of carbon monoxide sufficient to convert said nickel(II) complex reactant to the corresponding inventive acyl nickel(II) complex. Although carbonylation can occur at higher or lower temperatures, generally the reaction is conducted with a temperature in the range of about $-50°$ C. to about $100°$ C., preferably about $0°$ C. to about $50°$ C. Although the carbonylation can occur at higher or lower pressures, the reaction is generally carried out under an atmosphere consisting essentially of carbon monoxide at a pressure in the range of about 1 to about 1000 psig, preferably about 5 to about 200 psig. While longer or shorter reaction times can be employed, generally the reaction time is in the range of about 1 minute to about 24 hours, preferably about 2 minutes to about 2 hours.

In the carbonylation reaction, the amount of solvent employed is generally that which will insure that the nickel(II) complex reactant is in solution at the reaction temperature. The amount, and thus the pressure of carbon monoxide necessary for optimum production of the acyl nickel(II) product under specific conditions can be readily determined by one skilled in the art by trying various pressures. Generally progress of the reaction is evidenced by a drop in the pressure in the reactor.

In the carbonylation, more than one nickel(II) complex can be employed; but, this of course increases the chance for competing reactions and can render recovery of product more difficult.

Regardless of whether the trans-halo(acyl)bis(triethylphosphine)nickel(II) is prepared by acylation or carbonylation the product once prepared can then be recovered using any suitable techniques conventionally employed by those skilled in the art for recovering and purifying products contained in a diluent, i.e. precipitation, filtration and washing; or evaporation in vacuo, separation of impurities by chromatography, and recrystallization. It is thus convenient if the solvent employed is one in which the product is relatively insoluble at a temperature on the order of about $-20°$ C. to about $-80°$ C. or alternatively if the solvent is sufficiently volatile that the product can be isolated by solvent evaporation at a temperature which does not adversely affect the product.

The acyl nickel(II) complexes of this invention, like many of the compounds employed as reactants in preparing them, are sensitive to oxygen and/or water to varying degrees. Therefore, the preparation and use of these complexes should be conducted under an inert atmosphere, for example in a recirculating-atmosphere drybox providing an inert atmosphere such as argon.

The nickel(II) complexes of this invention can be used in a catalyst system for oligomerizing monoolefins to products such as dimers. The catalyst system employed in the oligomerization comprises at least one of the acyl nickel(II) complexes of the instant invention and at least one organoaluminum halide compound represented by the formula R''$_n$AlX$_{3-n}$, wherein each R'' is a hydrocarbyl radical having from 1 to 20 carbon atoms; each X is a halogen; and n is 1, 1.5, or 2.

Some specific examples of organoaluminum halide components of the catalyst system are: methylaluminum dichloride, dimethylaluminum chloride, diethylaluminum bromide, ethylaluminum dibromide, vinylaluminum diiodide, dibutylaluminum chloride, phenylaluminum dibromide, dibenzylaluminum chloride, 4-tolylaluminum dichloride, dodecylaluminum dibromide, methylaluminum sesquichloride, and the like and mixtures of any two or more thereof. Presently preferred aluminum compounds are organoaluminum halides containing hydrocarbon radicals having 1 to 6 carbons, such as methylaluminum sesquichloride.

The catalyst components can be combined in any suitable proportions. Generally they are combined in proportions in a range of 0.5:1 to about 20:1 moles of an organoaluminum halide per mole of nickel complex. Catalyst poisons in the system can be scavenged by employing even greater proportions of the organoaluminum halide compound.

The catalyst system is prepared by combining the first and second components of the catalyst-forming admixture under suitable conditions of time and temperature which permit the active catalyst to be formed. The two components of the catalyst system can be mixed at any suitable temperature. Generally the catalyst is prepared at a temperature in the range of about −80° to about 100° C. for a period of time ranging from a few seconds up to several hours in the presence of a diluent in which both of the catalyst-forming components are at least partially soluble. Any diluent is suitable that is an inert liquid under the reaction conditions. Examples of suitable solvents or diluents are benzene, cyclohexane, chlorobenzene, methylene chloride, ethylene chloride, and the like. However, halogenated diluents are preferred. The forming of the catalyst system by admixing the two components is generally carried out in an inert atmosphere and in the substantial absence of air or moisture. After the catalyst system is formed, it need not be isolated but can be added directly to the reaction zone as a solution or suspension in its preparation medium. If desired, the components used to form the catalyst system can be separately added, in any order, to the reaction zone either in the presence or absence of the feed olefin.

Any suitable monoolefin can be oligomerized employing the just-described catalyst system. Generally, the monoolefins oligomerized include hydrocarbyl cyclic monoolefins having up to and including 12 carbon atoms per molecule and hydrocarbyl acyclic monoolefins having from 2 to 12 carbon atoms, inclusive, where the acyclic monoolefin can be a terminal or an internal olefin, branched or unbranched. Examples of suitable monoolefins include, for example, ethylene, propylene, butene-1, butene-2, pentene-1, pentene-2, cyclopentene, cyclohexene, 3,4,5-trimethylcyclohexene, 3-methylbutene-1, cycloheptene, hexene-2, heptene-1, cyclooctene, 4,4-dimethylheptene-2, decene-1, dodecene-1, and the like, and mixtures of any two or more thereof. The preferred monoolefins are those hydrocarbons having from 2 to 12 carbon atoms and no branching on a doubly bonded carbon.

The oligomerization of the monoolefin or mixture of monoolefins can take place at any suitable temperature. Generally the temperature is within the range of about −80° to about 200° C., and preferably within the range of about −10° to about 50° C. The reaction is carried out with the diluent in the liquid phase. Also any suitable pressure can be employed. Normally, it is desirable to carry out the dimerization reaction under pressures ranging from about 0 psig up to about 2000 psig and preferably 20–50 psig. The oligomerization can be carried out in the presence of a diluent such as that used for the catalyst preparation if desired. The time of contact of the olefin with the catalyst for the oligomerization of the olefin will vary depending upon the desired degree of conversion but generally will be within the range from about 0.1 minute to about 20 hours, preferably 5 to 120 minutes. The proportion of nickel complex to olefin feed in the reaction zone will generally be within the range of about 0.00001 to about 0.1 mole of nickel complex per mole of olefin feed.

Any conventional contacting technique can be utilized for the olefin oligomerization and batchwise or continuous operations can be utilized. After the desired degree of conversion of the olefin to the dimer, the products so formed can be separated and isolated by conventional means such as by fractionation, crystallization, adsorption, and the like. The unconverted feed material can be recycled to the reaction zone. If desired, the catalyst can be destroyed by treatment with suitable deactivating agents such as water or alcohol, prior to the separation of the products.

Without further elaboration, one skilled in the art using the preceding disclosure should be able to utilize the present invention to its fullest extent. The following preferred specific embodiments are, therefore, to be construed as merely illustrative, and not unduly limitative of the remainder of the specification and claims in any way whatsoever.

Unless it is indicated as otherwise the work described in the following examples was done at atmospheric pressure in a recirculating-atmosphere drybox providing an argon atmosphere.

Examples I–X illustrate the preparation of specific inventive acyl nickel(II) complexes by acylation. Examples XI–XIII illustrate the preparation of specific inventive acyl nickel(II) complexes by carbonylation. Example XIV illustrates the employment of an inventive acyl nickel(II) complex in the oligomerization of a monoolefin.

EXAMPLE I

A 125 ml erlenmeyer flask was placed in a dry box and charged with a mixture of 0.55 g (2.0 mmols) of bis(1,5-cyclooctadiene)nickel(O), 5 ml of hexane and 0.48 g (4.0 mmols) of triethylphosphine. The mixture became homogeneous and was cooled to 5°–10° C. before the addition of 0.40 g (2.0 mmols) of 1-adamantanecarbonyl chloride. After the addition of the acyl chloride, the yellow solution became brown and golden brown platelets precipitated from the reaction mixture. The crystals were removed by suction filtration, washed with hexane and dried in vacuo to give 0.70 g of product [m.p. (air) 140°–142° C. dec.; m.p. (argon) 145°–147° C. dec.]. (The term "dec." as used in these examples is meant to indicate that there was decomposition with the melting.) The product was identified as trans-chloro(1-adamantanecarbonyl)bis(triethylphosphine)nickel(II) based upon the following elemental analysis:

|  | % C | % H |
|---|---|---|
| Theoretical | 55.95 | 9.19 |
| Found | 57.00 | 8.91 |

Further characterization of the above product was carried out on a sample recrystallized at −78° C. from ether containing about 1 ml of benzene. The bronze colored crystals which formed were isolated by suction filtration and were dried to a weight of 0.49 g [m.p. (argon) 148°–149° C. dec.]. This material was identified as trans-chloro(1-adamantanecarbonyl)bis(triethylphosphine)nickel(II) based upon the following elemental analysis:

|  | % C | % Ni |
| --- | --- | --- |
| Theoretical | 55.95 | 11.89 |
| Found | 56.31 | 11.4 |

EXAMPLE II

A small glass container equipped with a magnetic stirring bar was placed in a dry box and charged with a mixture of 0.55 g (2.0 mmols) of bis(1,5-cyclooctadiene)nickel(O), 10 ml of hexane and 0.47 g (4.0 mmols) of triethylphosphine. After cooling this mixture to 0° C., a 0.24 g (2.0 mmols) sample of pivaloyl chloride dissolved in 5 ml of cold hexane was added and the mixture was stirred at ambient temperature before cooling to −78° C. The red-brown platelets which formed were removed by suction filtration and dried to give 0.55 g of product [m.p. (argon): 73°–74° C. dec.]. The product was identified as trans-chloro(pivaloyl)bis(triethylphosphine)nickel(II) based upon the following elemental analysis:

|  | % C | % H | % Ni |
| --- | --- | --- | --- |
| Theoretical | 49.13 | 9.46 | 14.13 |
| Found | 49.39 | 9.76 | 14.43 |

EXAMPLE III

A small glass container equipped with a magnetic stirring bar was placed in a dry box and charged with 20 ml of hexane and 0.35 g (2.0 mmols) of 4-chlorobenzoyl chloride. To this solution was added dropwise a homogeneous mixture of 0.55 g (2.0 mmols) of bis(1,5-cyclooctadiene)nickel(O) and 0.47 g (4.0 mmols) of triethylphosphine in 10 ml of hexane. The resulting orange-red reaction mixture was cooled to −78° C. and the orange crystalline reaction product was removed by suction filtration and dried to give 0.63 g of product [m.p. (argon): 101°–110° C.]. An additional 0.04 g of product was obtained from the filtrate to give a total yield of 0.67 g. A sample recrystallized from ether gave the following analysis consistent with that expected for trans-chloro(4-chlorobenzoyl)bis(triethylphosphine)nickel(II):

|  | % C | % H |
| --- | --- | --- |
| Theoretical | 48.55 | 7.29 |
| Found | 48.56 | 7.34 |

EXAMPLE IV

A small glass container equipped with a magnetic stirring bar was placed in a dry box and charged with 20 ml of hexane and 0.35 g (2.0 mmols) of 3-chlorobenzyl chloride. To this solution was added in a dropwise fashion a homogeneous mixture of 0.55 g (2.0 mmols) of bis(1,5-cyclooctadiene)nickel(O) and 0.47 g (4.0 mmols) of triethylphosphine in 10 ml of hexane. During a period of 10 minutes at 25° C., the solution turned to a red-brown color and a tan precipitate formed. After removal of this precipitate by filtration, the filtrate was cooled to −78° C. to give 0.57 g of an orange-brown solid [m.p. (argon): 76°–82° C.]. Recrystallization from ether gave 0.17 g of orange crystals [m.p. (argon): 80°–86° C.]. An additional 0.10 g of orange crystals was isolated from the mother liquor. The elemental analysis approximates that expected trans-chloro(3-chlorobenzoyl)bis(triethylphosphine)nickel(II):

|  | % C | % H |
| --- | --- | --- |
| Theoretical | 48.55 | 7.29 |
| Found | 45.33 | 7.04 |

EXAMPLE V

A small glass container equipped with a magnetic stirring bar was placed in a dry box and charged with 2.8 g (20 mmols) of benzoyl chloride in 50 ml of hexane. To this solution was added in a dropwise fashion a homogeneous mixture of 5.5 g (20 mmols) of bis(1,5-cyclooctadiene)nickel(O) and 4.8 g (40 mmols) of triethylphosphine in 20 ml of hexane. A precipitate that formed on mixing was dissolved by the addition of 5–10 ml of acetonitrile. The solution was cooled to −78° C. and the orange crystals which precipitated were recovered by suction filtration. The orange crystals were dried in vacuo and subsequently combined with another crop of crystals from the filtrate to give a yield of 6.83 g. Recrystallization of the product from ether at −78° C. gave 4.73 g of product (m.p. 73.5°–75° C.). The elemental analysis was consistent with that expected for trans-chloro(benzoyl)bis(triethylphosphine)nickel(II):

|  | % C | % H |
| --- | --- | --- |
| Theoretical | 52.39 | 8.10 |
| Found | 52.58 | 8.34 |

EXAMPLE VI

A small glass container equipped with a magnetic stirring bar was placed in a dry box and charged with 0.55 g (2.0 mmols) of bis(1,5-cyclooctadiene)nickel(O) and 0.47 g (4.0 mmols) of triethylphosphine dissolved in 10 ml of hexane. To this solution was slowly added 0.27 g (2.0 mmols) of 3,3-dimethylbutanoyl chloride dissolved in 5 ml of hexane. The solution was filtered and the filtrate was concentrated in vacuo and then cooled to −78° C. to cause the precipitation of about 0.31 g of orange crystals. An additional 0.29 g of orange crystals was isolated from the mother liquor to give a total yield of 0.60 g (m.p. 100°–101° C.). The elemental analysis was consistent with the structure trans-chloro(3,3-dimethylbutanoyl)bis(triethylphosphine)nickel(II):

|  | % C | % H | %Ni |
| --- | --- | --- | --- |
| Theoretical | 50.32 | 9.62 | 13.67 |
| Found | 51.36 | 10.11 | 13.80 |

EXAMPLE VII

A small glass container was placed in a dry box and charged with a mixture of 0.35 g (2.0 mmols) of 2-chlorobenzoyl chloride in 20 ml hexane. To this solution was added in a dropwise manner a homogeneous mixture of 0.55 g (2.0 mmols) of bis(1,5-cyclooctadiene)nickel(O) and 0.47 g (4.0 mmols) of triethylphosphine in 10 ml of hexane. The solution became orange-red in color and on cooling to −78° C. red-brown crystals precipitated. This product was recovered by suction filtration and dried in vacuo to a weight of 0.62 g [m.p. (argon) 78°–80° C. with decarbonylation]. The elemental analysis approximates that expected for trans-chloro(2-chlorobenzoyl)bis(triethylphosphine)nickel(II):

|  | % C | % H |
|---|---|---|
| Theoretical | 48.55 | 7.29 |
| Found | 42.76 | 6.82 |

EXAMPLE VIII

A small glass container was placed in a dry box and charged with a mixture of 0.16 g (2.0 mmols) of acetyl chloride in 20 ml hexane. To this solution was added in a dropwise manner a homogeneous mixture of 0.55 g (2.0 mmols) of bis(1,5-cyclooctadiene)nickel(O) and 0.47 g (4.0 mmols) of triethylphosphine in 10 ml of hexane. The solution became yellow-brown in color and was cooled to −78° C. No crystals of trans-chloro(acetyl)bis(triethylphosphine)nickel(II) precipitated until the reaction mixture was concentrated in the cold to about 10 ml and rechilled to about −78° C. Crystallization was induced by scratching the inner wall of the reactor vessel with a solid glass rod. The resulting orange-brown crystals were recovered by suction filtration of the cold reaction mixture but on warming to 25° C., the product melted on the fritted glass filter and gradually decomposed. Structure verification was based on an infrared spectrum with the following characteristic absorptions (cm$^{-1}$): 2950 vs, 1980 vw, 1920 vw, 1640 vs, 1455 s, 1410 ms, 1395 m, 1320 m, 1250 mw, 1065 ms, 1040 vs, 1010 mw, 956 w, 887 mw, 767 vs, 737 w, 724 s, 708 w. This pattern of infrared absorptions is consistent with the proposed structure trans-chloro(acetyl)bis(triethylphosphine)nickel(II).

EXAMPLE IX

A small glass container equipped with a magnetic stirring bar was placed in a dry box and charged with 0.74 g (4.0 mmols) of benzoyl bromide in 5 ml of ether at 25° C. To this solution was added dropwise a homogeneous mixture of 1.10 g (4.0 mmols) of bis(1,5-cyclooctadiene)nickel(O) and 0.94 g (8.0 mmols) of triethylphosphine in 5 ml of hexane. The mixture assumed a cloudy red-brown appearance until about ⅔ of the Ni(O) reagent had been added at which point the reaction mixture warmed and became a clear dark brown solution. After addition was complete, the solution was filtered and the filtrate was cooled to −70° C. The resulting yellow-brown crystals were suction filtered, washed with cold hexane and dried to give 0.66 g of product. Recrystallization from ether at −70° C. gave 0.36 g (m.p. 77°–80° C.) of yellow-brown crystals. The elemental analysis is consistent with that expected for trans-bromo(benzoyl)bis(triethylphosphine)nickel(II):

|  | % C | % H |
|---|---|---|
| Theoretical | 47.54 | 7.35 |
| Found | 48.28 | 7.25 |

EXAMPLE X

A small glass container equipped with a magnetic stirring bar was placed in a dry box and charged with 0.51 g (4.0 mmols) of benzoyl fluoride in 5 ml of ether at 25° C. To this solution was added in a dropwise manner a yellow-brown solution of 1.10 g (4.0 mmols) of bis(1,5-cyclooctadiene)nickel(O) and 0.94 g (8.0 mmols) of triethylphosphine in a mixture of 5 ml hexane and 2 ml of ether. The resulting homogeneous mixture was cooled to −70° C. and filtered to remove a very small amount of bis(1,5-cyclooctadiene)nickel(O). The filtrate was concentrated in vacuo and cooled to −70° C. Brown crystals were recovered by suction filtration, washed with cold hexane and dried to give 0.64 g (m.p. 55.5°–57° C.) of trans-fluoro(benzoyl)bis(triethylphosphine)nickel(II). The filtrate was stored at −35° C. for about 64 hours to give an additional 0.51 g of product (m.p. 53°–57° C.). Structure verification was based on an infrared spectrum with the following characteristic absorptions (cm$^{-1}$): 2930 vs, 1605 s, 1575 m, 1455 s, 1415 mw, 1375 m, 1300 w, 1255 w, 1240 w, 1180 w, 1145 mw, 1135 mw, 1075 w, 1035 s, 1005 w, 876 s, 783 mw, 767 s, 727 s, 701 s, 676 mw. This pattern of infrared absorptions is consistent with the proposed structure trans-fluoro(benzoyl)bis(triethylphosphine)nickel(II).

EXAMPLE XI

A small Diels-Alder pressure tube was placed in a dry box and charged with 0.81 g (2.0 mmols) of trans-chloro(phenyl)bis(triethylphosphine)nickel(II) and 5 ml of hexane. The tube was capped and removed from the dry box. The tube was partially flushed with carbon monoxide, pressured to 15 psig with carbon monoxide and then was allowed to stand at ambient temperature for about 14 hours. During this period of time orange crystals had precipitated from the solution. After venting the system, the tube was returned to the dry box, cooled to −72° C. and the orange crystals were removed by suction filtration, washed with ether and dried in vacuo. The orange crystals weighed 0.70 g and exhibited a melting point of 73°–75° C. The orange colored product possessed an infrared spectrum (Nujol) which was identical to that exhibited by the trans-chloro(benzoyl)bis(triethylphosphine)nickel(II) prepared (see Example V) by the reaction of benzoyl chloride with a mixture of bis(1,5-cyclooctadiene)nickel(O) and triethylphosphine in hexane solution.

EXAMPLE XII

A small aerosol compatibility bottle equipped with a magnetic stirring bar was placed in a dry box and charged with 1.05 g (2.38 mmols) of trans-chloro(2-chlorophenyl)bis(triethylphosphine)nickel(II) and 10 ml of hexane. The bottle was capped and removed from the dry box. The bottle was pressured to 200 psig with carbon monoxide and on stirring the solution turned orange, absorbed some carbon monoxide and an orange colored precipitate appeared. After standing at ambient temperature for about 14 hours, the reactor bottle was vented, returned to the dry box and cooled to −20° C. to complete the precipitation. An orange-colored precipitate (0.80 g) contaminated with black and green impurities was isolated by suction filtration and exhibited an infrared spectrum (Nujol) identical to that of the trans-chloro(2-chlorobenzoyl)bis(triethylphosphine)-nickel(II) prepared by contacting 2-chlorobenzoyl chloride with a mixture of bis(1,5-cyclooctadiene)nickel(O) and triethylphosphine (see Example VII).

In an attempt to purify the above product, the solid was dissolved in ether and filtered to remove impurities. During this time the ether solution bubbled perhaps due to decarbonylation and on cooling the ethereal mixture to −72° C., a mixture of orange and yellow crystals precipitated. The entire mixture was transferred to an aerosol compatibility bottle, pressured to 200 psig with carbon monoxide and allowed to stand at ambient temperature for about 64 hours. The yellow solution was decanted and on cooling to −72° C., orange crystals (0.1 g, m.p. 84°-86.5° C.) separated from solution. These orange crystals exhibited an infrared spectrum (Nujol) identical to that of the trans-chloro(2-chlorobenzoyl)bis(triethylphosphine)nickel(II) of Example VII and gave the following elemental analysis:

|  | % C | % H | % Cl | % Ni |
| --- | --- | --- | --- | --- |
| Theoretical | 48.55 | 7.29 | 15.09 | 12.49 |
| Found | 49.75 | 7.96 | 15.38 | 12.71 |

The orange crystalline product decarbonylated completely on heating to about 105° C. to yield trans-chloro(2-chlorophenyl)bis(triethylphosphine)nickel(II) with a melting point in the range of 85°-88° C.

EXAMPLE XIII

A small Diels-Alder pressure tube equipped with a magnetic stirring bar was placed in a dry box and charged with 0.44 g (1.0 mmol) of trans-chloro(3-chlorophenyl)bis(triethylphosphine)nickel(II) and 5 ml of hexane. The tube was capped, removed from the dry box and pressured to 16 psig with carbon monoxide. On stirring a rapid uptake of carbon monoxide was evidenced by the decrease in pressure to about 3 psig in a few minutes. The tube was repressured to 16 psig with carbon monoxide and allowed to stand at ambient temperature for about 14 hours. During this time period orange crystals precipitated from solution. After venting the system, the tube was returned to the dry box, cooled to −72° C. and orange crystals were removed by suction filtration, washed with cold hexane and dried in vacuo. The orange crystals weighed 0.43 g [m.p. (under argon) 83°-88° C.] and possessed an infrared spectrum (Nujol) identical to that exhibited by the sample of trans-chloro(3-chlorobenzoyl)bis(triethylphosphine)nickel(II) prepared in Example IV. The orange crystals have the following elemental analysis which is consistent with the above proposed structure:

|  | % C | % H | % Cl | % Ni |
| --- | --- | --- | --- | --- |
| Theoretical | 48.55 | 7.29 | 15.09 | 12.49 |
| Found | 49.20 | 7.85 | 15.64 | 12.89 |

EXAMPLE XIV

An oven-dried 9 oz. glass bottle reactor equipped with a magnetic stirring bar was charged with a mixture of 0.05 g (0.1 mmol) of trans-chloro(4-chlorobenzoyl)-bis(triethylphosphine)nickel(II) and 20 ml of chlorobenzene. The bottle was capped and then sequentially flushed for one hour intervals with argon and propylene. The capped bottle reactor was then cooled in an ice-salt bath for 5 minutes before pressuring the system to 30 psig with propylene. The system was maintained in the cold bath, vented to 5 psig, and 0.70 ml (0.70 mmol) of methylaluminum sesquichloride was added by syringe as a 1 M chlorobenzene solution to the stirred reaction mixture. The bottle was pressured to and maintained at 30 psig with propylene and the stirred reaction mixture was kept in the cold bath for one hour. At this time the bottle was vented and 10 ml of saturated aqueous sodium chloride solution was added. The aqueous and organic phases were separated and the aqueous phase was extracted one time with 5 ml of chlorobenzene. The combined organic phases were dried over anhydrous magnesium sulfate. Distillation of the dried organic phase gave 29.35 g of colorless liquid with a boiling range of 60°-68° C.

A 2.0 g sample of the above liquid was hydrogenated over 0.1 g of PtO$_2$ under 20-90 psig of H$_2$ for 18 hours. The hydrogenated product was examined by glpc on a 20′×⅛″ isoquinoline column at 25° C. to give the following analysis:

| Component | Area % |
| --- | --- |
| 2,3-dimethylbutane | 19.8 |
| 2-methylpentane | 66.9 |
| n-hexane | 13.3 |

This demonstrates that dimers were formed and it further indicates the skeletal structure of the dimers.

The terms and expressions employed in this disclosure are used as terms of description and are not intended to be unduly limiting. There is no intention in the use of such terms and expressions of excluding any equivalents of features shown and described or portions thereof. Further, it should be recognized that various modifications are possible within the scope of the following claims.

We claim:

1. A process for oligomerizing monoolefins comprising contacting under suitable reaction conditions at least one said monoolefin with a catalyzing amount of a catalyst system comprising (1) at least one organoaluminum halide compound having the formula R″$_n$AlX$_{3−n'}$ wherein each R″ is a hydrocarbyl radical having from 1 to 20 carbon atoms; each X is a halogen; and n is 1, 1.5, or 2; and (2) at least one acyl nickel complex having the formula

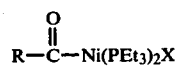

wherein X is a halogen; PEt$_3$ is triethylphosphine; and R is selected from the group consisting of alkyl hydrocarbon radicals containing 6 to 12 carbon atoms; substituted aryl radicals containing 6 to 12 carbon atoms and having as the only non-hydrocarbon substituents 1 or 2 halogens selected from fluorine, chlorine, and bromine bonded to the aromatic portion of the aryl radical; and substituted aralkyl radicals containing 7 to 12 carbon atoms and having as the only nonhydrocarbon substituents one or more halogens selected from fluorine, chlorine and bromine bonded to the aromatic portion of the aralkyl radical.

2. A process according to claim 1 wherein the mole ratio of said organoaluminum halide compound to said acyl nickel complex is in the range of about 0.5:1 to about 20:1 and the mole ratio of said nickel complex to said monoolefin is in the range of about 0.00001:1 to about 0.1:1.

3. A process according to claim 2 wherein said at least one monoolefin is selected from monoolefins having 2 to 12 carbon atoms and no branching on a doubly bonded carbon atom.

4. A process according to claim 3 wherein said contacting is carried out in the temperature range of about −80° to about 200° C. and in the pressure range of about 0 psig to about 2000 psig.

5. A process according to claim 4 wherein said monoolefin is propylene.

6. A process according to claim 5 wherein said acyl nickel complex is trans-chloro(4-chlorobenzoyl)bis(triethylphosphine)nickel(II) and said organoaluminum halide compound is methylaluminum sesquichloride.

7. A process according to claim 4 wherein said at least one nickel complex is selected from the group consisting of trans-chloro(1-adamantanecarbonyl)bis(triethylphosphine)nickel(II), trans-chloro(pivaloyl)bis(triethylphosphine)nickel(II), trans-chloro(4-chlorobenzoyl)bis(triethylphosphine) nickel(II), trans-chloro(3-chlorobenzoyl)bis(triethylphosphine)nickel(II), trans-chloro(benzoyl)bis(triethylphosphine)nickel(II), trans-chloro(3,3-dimethylbutanoyl)bis(triethylphosphine)nickel(II), trans-chloro(2-chlorobenzoyl)bis (triethylphosphine)nickel(II), trans-chloro(acetyl)bis(triethylphosphine) nickel(II), trans-bromo(benzoyl)bis(triethylphosphine)nickel(II), trans-fluoro (benzoyl)bis(triethylphosphine)nickel(II), and trans-chloro(1-naphthoyl)bis (triethylphosphine)nickel(II).

8. A process according to claim 7 wherein said at least one organoaluminum halide compound is selected from the group consisting of methylaluminum dichloride, dimethylaluminum chloride, diethylaluminum bromide, ethylaluminum dibromide, vinylaluminum diiodide, dibutylaluminum chloride, phenylaluminum dibromide, dibenzylaluminum chloride, 4-tolylaluminum dichloride, dodecylaluminum dibromide, and methylaluminum sesquichloride.

9. A process according to claim 8 wherein said monoolefin is propylene.

10. A process according to claim 9 wherein said at least one organoaluminum halide compound is methyl aluminum sesquichloride.

* * * * *